US012465529B2

(12) United States Patent
Minami

(10) Patent No.: US 12,465,529 B2
(45) Date of Patent: Nov. 11, 2025

(54) DISPOSABLE DIAPER

(71) Applicant: DAIO PAPER CORPORATION, Ehime (JP)

(72) Inventor: Takeshi Minami, Tochigi (JP)

(73) Assignee: Daio Paper Corporation, Ehime (JP)

( * ) Notice: Subject to any disclaimer, the term of this patent is extended or adjusted under 35 U.S.C. 154(b) by 335 days.

(21) Appl. No.: 18/265,101

(22) PCT Filed: Jan. 26, 2022

(86) PCT No.: PCT/JP2022/002762

§ 371 (c)(1),
(2) Date: Jun. 2, 2023

(87) PCT Pub. No.: WO2022/176533

PCT Pub. Date: Aug. 25, 2022

(65) Prior Publication Data

US 2024/0016668 A1 Jan. 18, 2024

(30) Foreign Application Priority Data

Feb. 17, 2021 (JP) ................................ 2021-023326

(51) Int. Cl.
*A61F 13/15* (2006.01)
*A61F 13/49* (2006.01)
*A61F 13/511* (2006.01)

(52) U.S. Cl.
CPC .... *A61F 13/49001* (2013.01); *A61F 13/4902* (2013.01); *A61F 13/511* (2013.01); *A61F 2013/49033* (2013.01)

(58) Field of Classification Search
CPC ............ A61F 13/49001; A61F 13/4902; A61F 13/511; A61F 13/536; A61F 13/535; A61F 2013/530861

(Continued)

(56) References Cited

U.S. PATENT DOCUMENTS 8,975,466 B2 * 3/2015 R. Marcelo ......... A61F 13/4758 604/378

FOREIGN PATENT DOCUMENTS

JP 2017-60634 3/2017
JP 2018-51076 4/2018

(Continued)

OTHER PUBLICATIONS

International Search Report and the Written Opinion for PCT/JP2022/002762, dated Mar. 29, 2022.

*Primary Examiner* — Jacqueline F Stephens

(74) *Attorney, Agent, or Firm* — Andrus Intellectual Property Law, LLP

(57) ABSTRACT

A disposable diaper whose deformation while the wearer is walking, is suppressed to alleviate discomfort, first slits extend from ventral section to the front of crotch section in their side portions at a distance from and in parallel to first oblique parts, a second slit extends in parallel to straight parts, in the central part in the width direction of middle area of the crotch section, third slits extend at a distance from second oblique parts in the back of the crotch section in its side portions, with the back end of each third slit located outwards of its front end, fourth slits extend crossing each other in parallel to the second oblique parts, in the middle area of dorsal section, back ends of the first slits are located inwards of the straight parts, and front ends of the fourth slits are at a longitudinal distance from the back ends of the third slits.

10 Claims, 10 Drawing Sheets

(58) Field of Classification Search
USPC .................................. 604/380, 385.101, 379
See application file for complete search history.

(56) References Cited

FOREIGN PATENT DOCUMENTS

| | | |
|---|---|---|
| JP | 2019-216956 | 12/2019 |
| JP | 2020-065817 | 4/2020 |
| JP | 2020-192123 | 12/2020 |

* cited by examiner

[FIG.1]
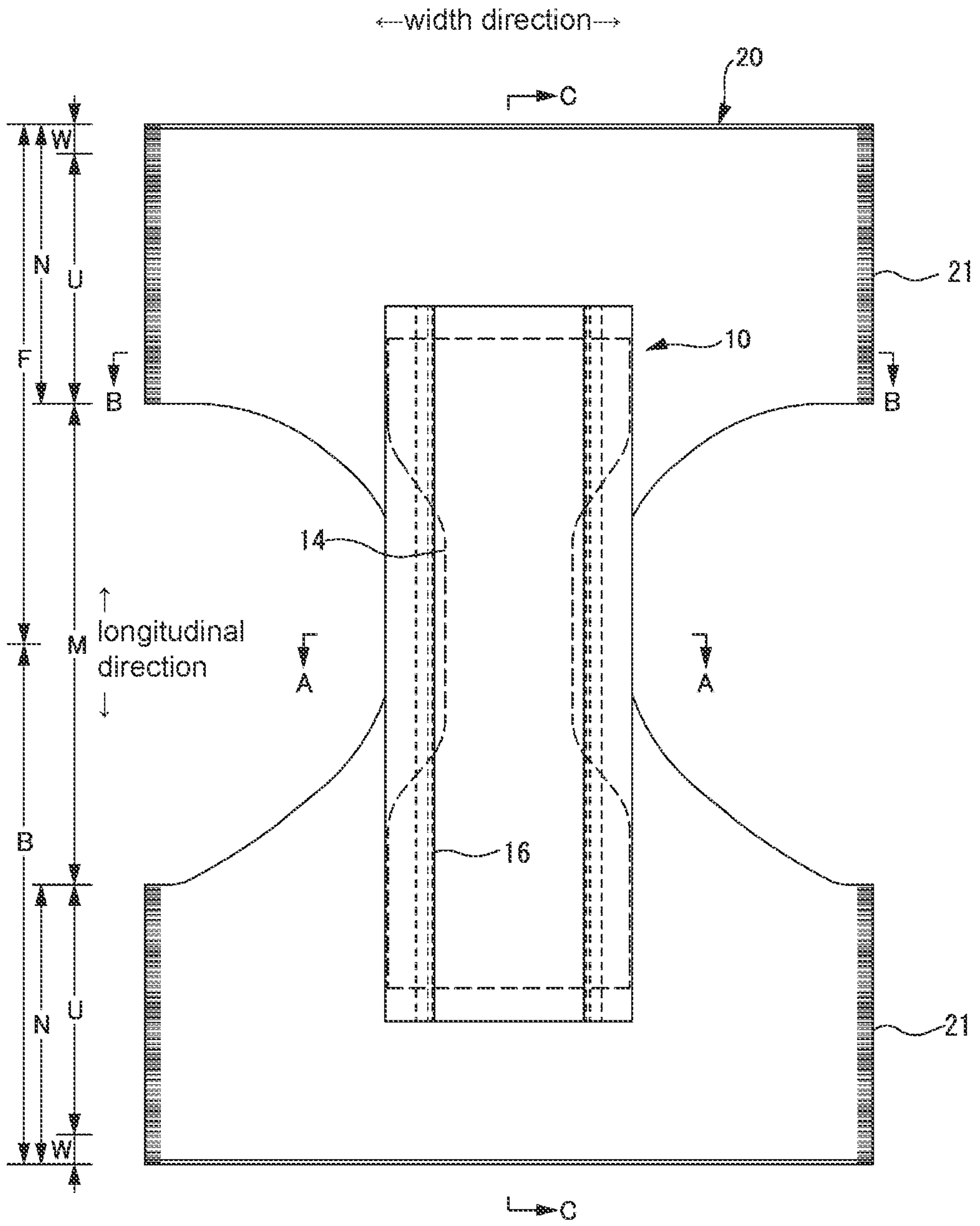

[FIG.2]
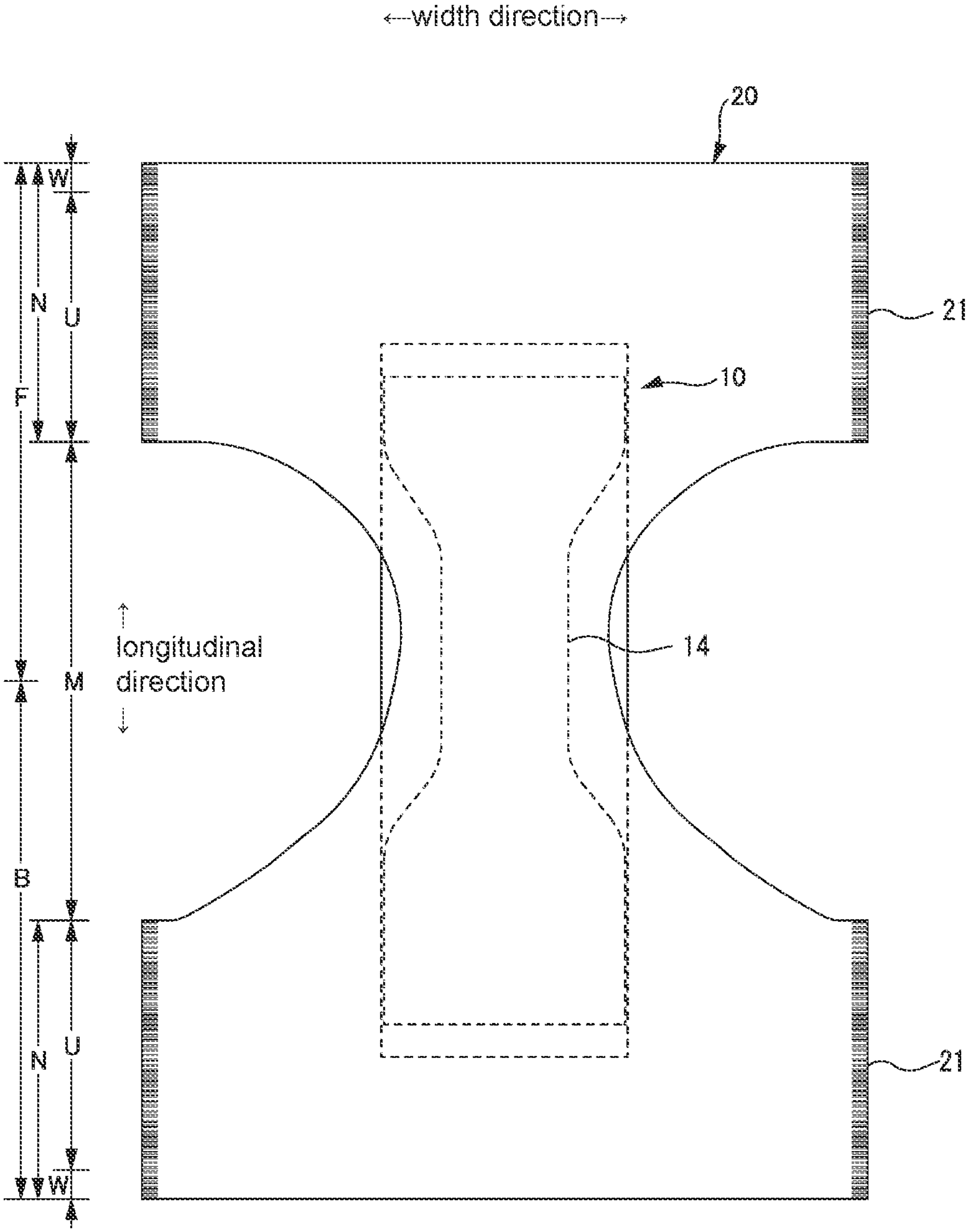

【FIG.3】
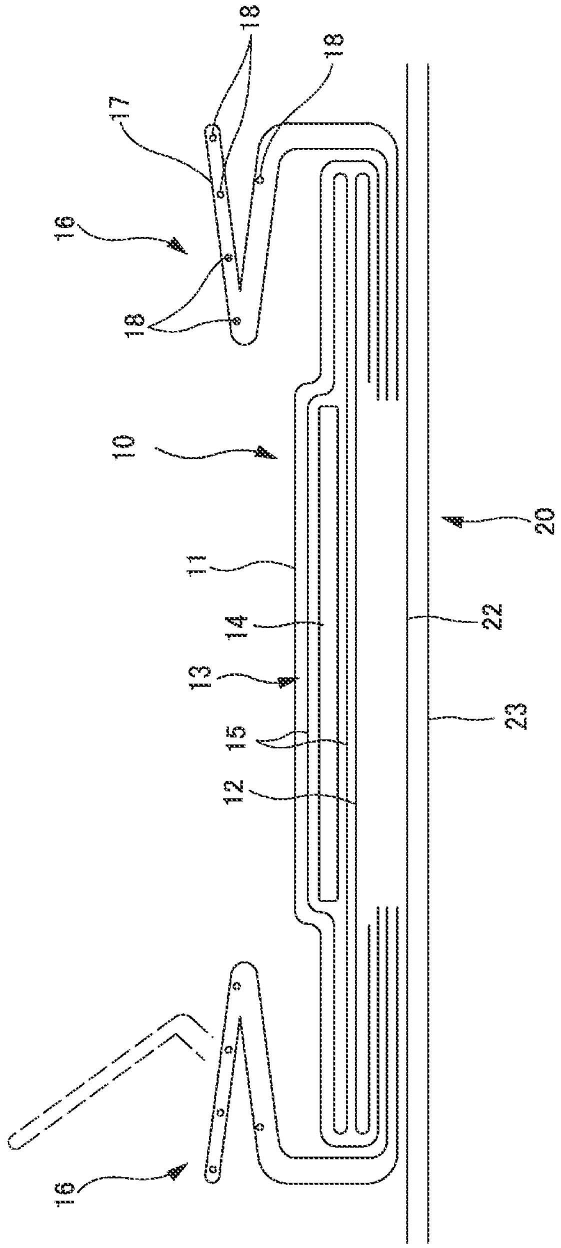

【FIG.4】
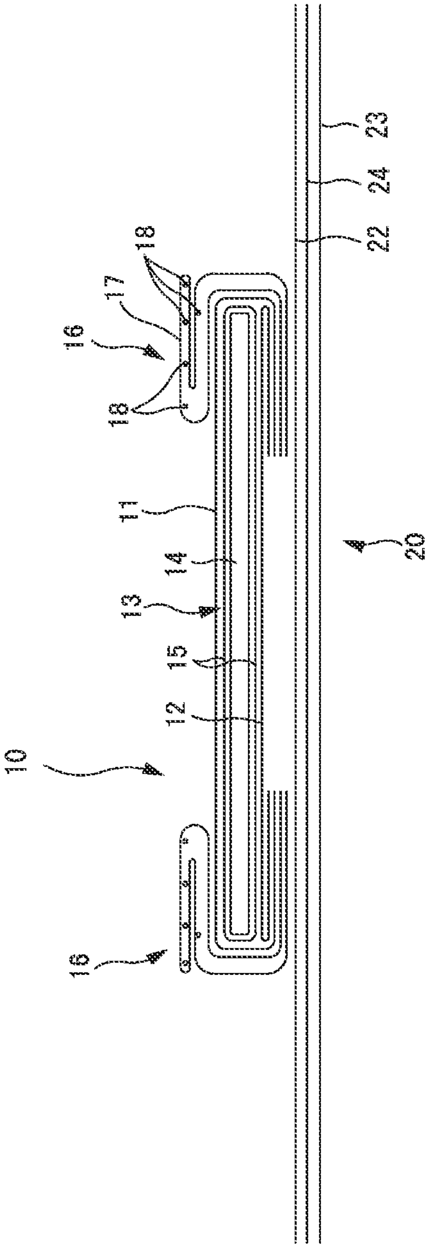

[FIG.5]
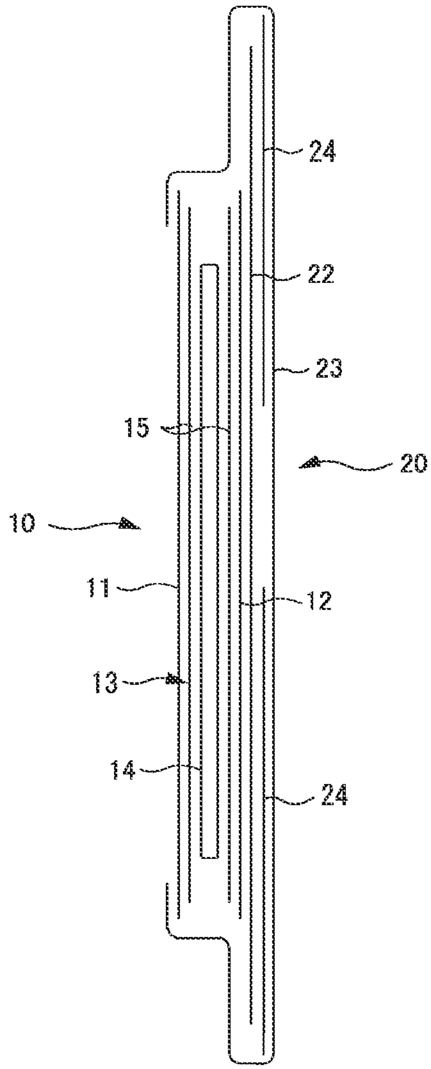

[FIG.6]
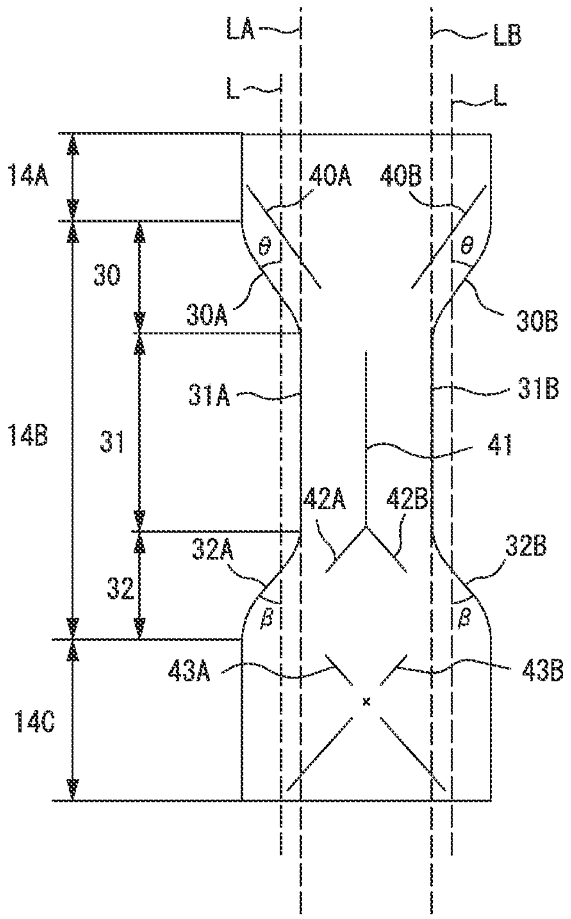

[FIG.7]
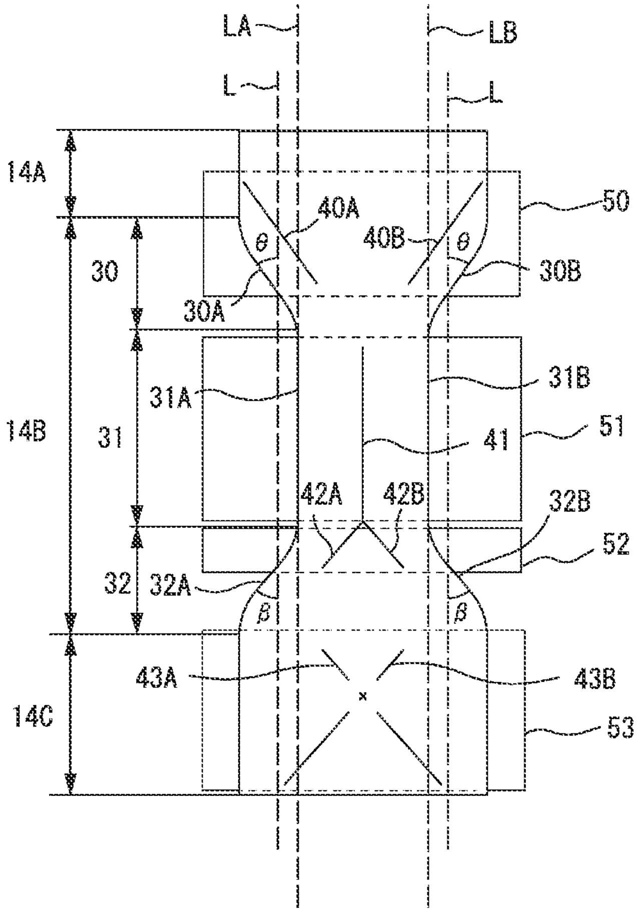

[FIG.8]
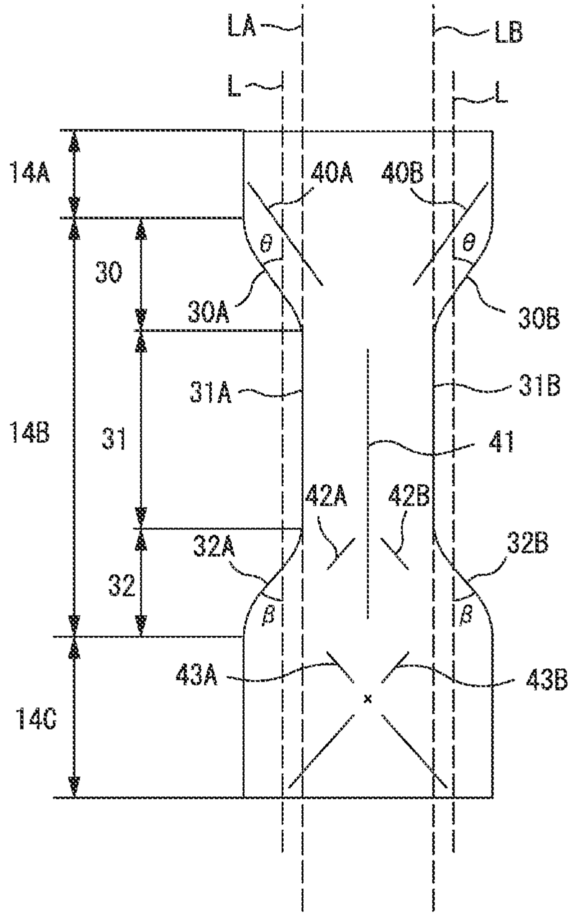

[FIG.9]
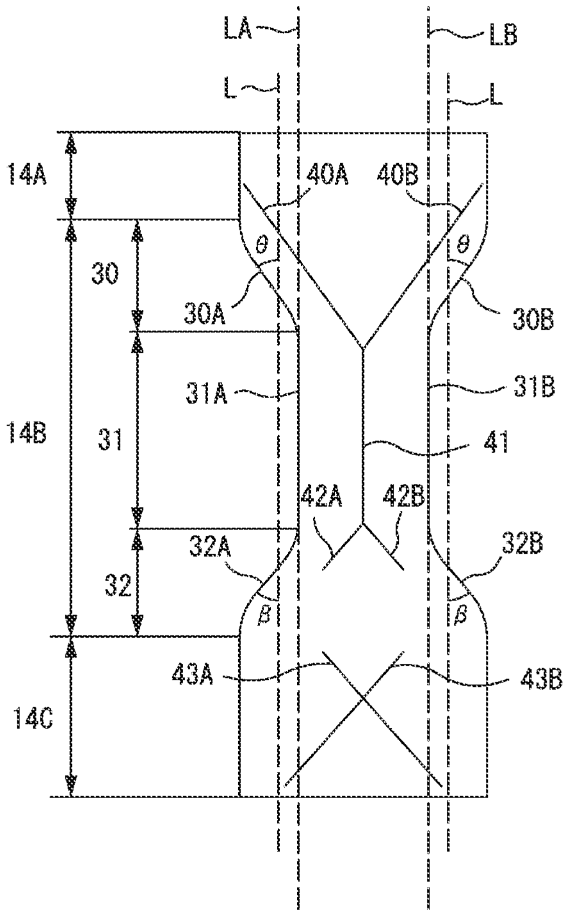

[FIG.10]
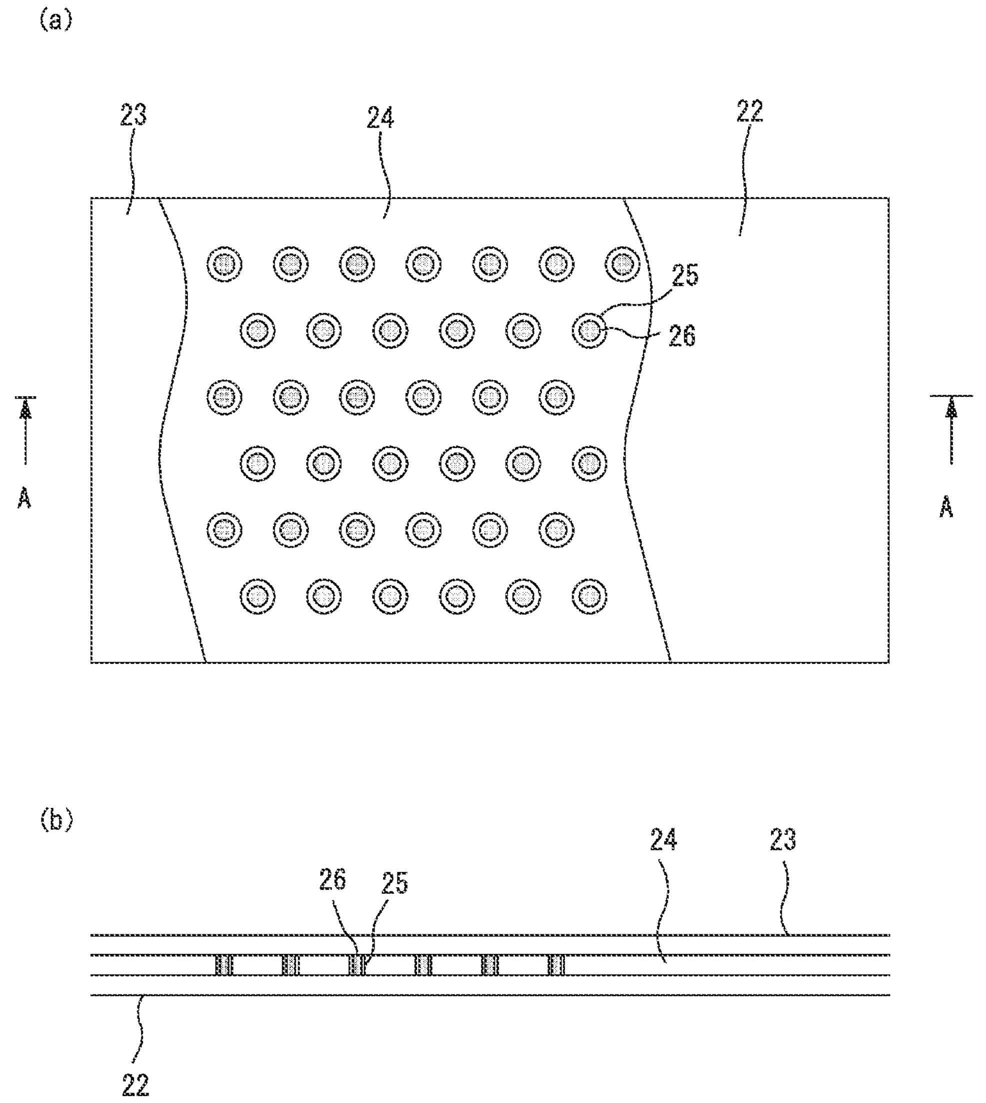

DISPOSABLE DIAPER

CROSS-REFERENCE TO RELATED APPLICATIONS

This application is the U.S. national stage application of International Application PCT/JP2022/002762, filed Jan. 26, 2022, which international application was published on Aug. 25, 2022, as International Publication WO 2022/176533 in the Japanese language. The International Application claims priority of Japanese Patent Application No. 2021-023326, filed Feb. 17, 2021. The international application and Japanese application are both incorporated herein by reference, in entirety.

FIELD OF ART

The present invention relates to underpants-type disposable diapers, in particular, an absorbent body in the inner member of a disposable diaper.

BACKGROUND ART

There is conventionally known to provide, for alleviating discomfort felt by the wearer of a disposable diaper, a longitudinally extending slit in each of the side areas opposed in the width direction of the crotch region of the absorbent body, and a slit extending from the front end of each of the longitudinally extending slit, forward in the ventral region of the absorbent body along the groin and curving outwards in the width direction (Patent Publication 1).

There is also known to provide, for suppressing deformation of the absorbent body while the wearer is walking or the like, a pair of slits spaced apart from each other in the width direction and extending forward and outward in the width direction in the ventral region of the absorbent body (Patent Publication 2).

PRIOR ART PUBLICATION

Patent Publication

Patent Publication 1: JP 2019-216956 A
Patent Publication 2: JP 2020-065817 A

SUMMARY OF THE INVENTION

Problems to be Solved by the Invention

The means disclosed in Patent Publication 1, however, cannot suppress deformation of the dorsal region of the absorbent body while the wearer is walking or the like. Further, the slits cannot suppress large deformation in the crotch region of the absorbent body sufficiently, so that the discomfort felt by the wearer may not be alleviated sufficiently.

The means disclosed in Patent Publication 2, similarly to Patent Publication 1, cannot suppress deformation of the dorsal region of the absorbent body while the wearer is walking or the like. Also, the slits cannot suppress large deformation in the crotch region of the absorbent body sufficiently, so that the discomfort felt by the wearer may not be alleviated sufficiently.

It is therefore an object of the present invention to provide a disposable diaper in which the deformation of the absorbent body in its ventral region, crotch region, and dorsal region while the wearer is walking or the like, is suppressed to alleviate the discomfort felt by the wearer of the disposable diaper.

Solution to Problems

Solution to the above problem are as follows.

According to a first aspect, there is provided a disposable diaper including an inner member having a liquid-permeable top sheet, a liquid-impermeable under sheet, and an absorbent body interposed between the top sheet and the under sheet, and an outer member stretchable in its width direction and fixed on a surface of the inner member opposite to another surface thereof facing to a body of a wearer, wherein the absorbent body, as seen in plan view, has a rectangular ventral section facing a ventral portion of the wearer, a rectangular dorsal section facing a dorsal portion of the wearer, and a crotch section connecting the ventral section and the dorsal section, wherein each of side edges opposed in a width direction of a front area of the crotch section has a first oblique part extending from front backward and inward in the width direction, wherein each side edges opposed in a width direction of the back area of the crotch section has a second oblique part extending from back forward and inward in the width direction, wherein each of side edges opposed in a width direction of a middle area of the crotch section has a straight part extending from a back end of the first oblique part to a front end of the second oblique part, wherein a pair of first slits is provided from the ventral section to the front area of the crotch section in their side portions opposed in their width direction, at a distance from and in parallel to the first oblique parts, wherein a second slit is provided in parallel to the straight parts, in a central part in a width direction of the middle area of the crotch section, wherein a pair of third slits is provided at a distance from the second oblique parts, in the back part of the crotch section in its side portions opposed in the width direction, with a back end of each third slit located laterally outwards of its front end in the width direction, wherein a pair of fourth slits is provided crossing each other and in parallel to the second oblique parts, in a middle area in a width direction of the dorsal section, wherein back ends of the first slits are located inwards of the straight parts in a width direction of the absorbent body, and wherein front ends of the fourth slits are located at a longitudinal distance from the back ends of the third slits.

The second aspect is characterized in that, in the structure of the first aspect, a point of crossing of the fourth slits is located at a center of the width direction of the dorsal section, and wherein a length of each fourth slit backward of the point of crossing is longer than a length of the fourth slit forward of the point of crossing.

The third aspect is characterized in that, in the structure of the first or second aspect, a width in a minor axis direction of the second slit is larger than that of the first slits, that of the third slits, and that of the fourth slits.

The fourth aspect is characterized in that, in the structure of any one of the first to third aspect, the front ends of the third slits are connected to a back end of the second slit.

The fifth aspect is characterized in that, in the structure of any one of first to fourth aspect, an elastic member stretchable in its width direction is provided on a surface of the absorbent body opposite to another surface facing the body of the wearer, in at least one of positions facing to the first slits, the second slits, the third slits, and the fourth slits.

Effect of the Invention

The first aspect includes an inner member having a liquid-permeable top sheet, a liquid-impermeable under sheet, and an absorbent body interposed between the top sheet and the under sheet, and an outer member stretchable in its width direction and fixed on a surface of the inner member opposite to another surface facing a body of a wearer, the absorbent body, as seen in plan view, has a rectangular ventral section facing to the ventral portion of the wearer, a rectangular dorsal section facing the dorsal portion of the wearer, and a crotch section connecting the ventral section and the dorsal section, each of side edges opposed in the width direction of a front area of the crotch section has a first oblique part extending from front backward and inward in the width direction, each of side edges opposed in the width direction of a back area of the crotch section has a second oblique part extending from back forward and inward in the width direction, each of side edges opposed in the width direction of a middle area of the crotch section has a straight part extending from the back end of the first oblique part to the front end of the second oblique part, a pair of first slits is provided from the ventral section to the front area of the crotch section in their side portions opposed in their width direction, at a distance from and in parallel to the first oblique parts, a second slit is provided in parallel to the straight parts, in the central part in the width direction of the middle area of the crotch section, a pair of third slits is provided at a distance from the second oblique parts, in the back part of the crotch section in its side portions opposed in the width direction, with the back end of each third slit located laterally outwards of the front end in the width direction, a pair of fourth slits is provided crossing each other and in parallel to the second oblique parts, in the middle area in the width direction of the dorsal section, back ends of the first slits are located inwards of the straight parts in the width direction of the absorbent body, and the front ends of the fourth slits are located at a longitudinal distance from the back ends of the third slits. Accordingly, deformation of the absorbent body caused by force applied to the absorbent body while the wearer is walking or the like, is suppressed by the first to fourth slits being narrowed, and the discomfort felt by the wearer of a disposable diaper may be alleviated. Further, the bodily waste, such as urine, on the absorbent body may be kept from leaking out through the back ends of the third slits.

According to the second aspect, the point of crossing of the fourth slits is located at the center in the width direction of the dorsal section, and the length of each fourth slit backward of the point of crossing is longer than the length of the fourth slit forward of the point of crossing. Accordingly, in addition to the effect from the first aspect, the dorsal section of the absorbent body may effectively be caused to fit on the dorsal portion of the wearer.

According to the third aspect, the width in the minor axis direction of the second slit is larger than that of the first slits, that of the third slits, and that of the fourth slits. Accordingly, in addition to the effect from the first or second aspect, deformation of the crotch section of the absorbent body, which deforms the most while the wearer is walking or the like, may further be suppressed.

According to the fourth aspect, the front ends of the third slits are connected to the back end of the second slit. Accordingly, in addition to the effect from any one of the first to third aspect, deformation of the crotch section of the absorbent body, which deforms the most while the wearer is walking or the like, may further be suppressed.

According to the fifth aspect, an elastic member stretchable in its width direction is provided on the surface of the absorbent body opposite to the other surface facing the body of the wearer, in at least one of positions facing to the first slits, the second slits, the third slits, and the fourth slits. Accordingly, in addition to the effect from any one of the first to fourth aspect, the first to fourth slits may effectively be narrowed.

BRIEF DESCRIPTION OF THE DRAWINGS

FIG. 1 is a plan view of a disposable diaper showing its body-facing surface.

FIG. 2 is a plan view of the disposable diaper showing its surface opposite from the body-facing surface.

FIG. 3 is a cross-sectional view taken along lines A-A in FIG. 1.

FIG. 4 is a cross-sectional view taken along lines B-B in FIG. 1.

FIG. 5 is a sectional view taken along lines C-C in FIG. 1.

FIG. 6 is a plan view of an absorbent body showing its body-facing surface according to the first embodiment.

FIG. 7 is a plan view of an absorbent body showing its body-facing surface according to the second embodiment.

FIG. 8 is a plan view of an absorbent body showing its body-facing surface according to the third embodiment.

FIG. 9 is a plan view of the absorbent body showing its body-facing surface according to the fourth embodiment.

FIG. 10(*a*) is a partially-fragmented plan view of an outer member on its body-facing surface, and FIG. 10(*b*) is a cross-sectional view taken along lines A-A in FIG. 10(*a*).

EMBODIMENTS FOR CARRYING OUT THE INVENTION

As shown in FIGS. 1 and 2, the disposable diaper is composed of an inner member 10 and an outer member 20 fixed to the surface of the inner member 10 opposite from its body-facing surface.

<Inner Member>

As shown in FIGS. 3 to 5, the inner member 10 is composed of a liquid-pervious top sheet 11 arranged on the side facing the body of the wearer, a liquid-impervious under sheet 12 arranged on the side opposite to the other side facing the body of the wearer, an absorbent element 13 interposed between the top sheet 11 and the under sheet 12, and a three-dimensional gather part 16 disposed in each of the side portions opposed in the width direction of the inner member 10.

Each of the side portions opposed in the width direction of the top sheet 11 turns around the corresponding side edges of the under sheet 12 and the absorbent element 13, toward the surface of the absorbent element 13 opposite from its body-facing surface. Each of the end portions opposed in the longitudinal direction of the top sheet 11 extends beyond the corresponding end of the absorbent element 13.

The top sheet 11 may preferably be perforated or imperforated nonwoven fabric, a porous plastic sheet, or the like. The raw material fibers constituting the nonwoven fabric may be synthetic fibers, such as polyolefin-based, including polyethylene or polypropylene, polyester-based, or polyamide-based fibers, recycled fibers, such as rayon or cupra, or natural fibers, such as cotton, and the nonwoven fabric may have been produced through suitable processing, such as spunlacing, spunbonding, thermal bonding, melt-blowing, or needle punching. Among these processing methods, the spunlacing is superior in imparting flexibility and draping properties, whereas the thermal bonding is superior in imparting bulkiness and softness. With a number of through holes formed through the top sheet 11, urine or the like may rapidly be absorbed, resulting in improved dry touch of the top sheet.

Each of the side portions opposed in the width direction of the under sheet 12 is folded onto its surface opposite from its body-facing surface and extends to the corresponding outer edge of the absorbent element 13. Each of the end portions opposed in the longitudinal direction of the under sheet 12 extends beyond the corresponding end of the absorbent element 13.

The under sheet 12 may be a liquid-impervious sheet of plastic, such as polyethylene or polypropylene, and those having moisture-permeability are preferably used recently for preventing dampness. Such liquid-impervious, moisture-permeable sheet may be a microporous sheet obtained by kneading an inorganic filler in a polyolefin-based resin, such as polyethylene or polypropylene, in a molten state, forming the resulting mixture into a sheet, and then uni- or biaxially drawing the sheet.

The absorbent element 13 is composed of an absorbent body 14 and a wrapping sheet 15 covering the absorbent body 14. In its spread state, the absorbent element 13 is in a rectangular shape.

The absorbent body 14 has a ventral section 14A corresponding to the ventral portion of the wearer, a crotch section 14B corresponding to the crotch portion of the wearer, and a dorsal section 14C corresponding to the dorsal portion of the wearer. The dimensions of the ventral section 14A, the crotch section 14B, and the dorsal section 14C may suitably be decided depending on the figure of the wearer, and the dimension in the width direction of the narrowest part of the crotch section 14B may preferably be 40 to 60% the dimension in the width direction of the ventral section 14A or the dorsal section 14C, and the dimension in the longitudinal direction of the crotch section 14B may preferably be 20 to 50% the dimension in the longitudinal direction of the absorbent body 14. This may cause the disposable diaper to fit the wearer.

The absorbent body 14 may be an accumulation of pulp fibers, an assembly of filaments, such as of cellulose acetate, or nonwoven fabric, to which a high-absorbent polymer may be mixed, fixed, or otherwise, as required.

The wrapping sheet 15 may be a liquid-pervious crepe paper for keeping the high-absorbent polymer mixed in the absorbent body 14 from leaking out.

Each three-dimensional gather part 16 has a fixed part fixed to the surface of the inner member 10 opposite from its body-facing surface in the corresponding side portion in the width direction, and a body part extending from the fixed part, around the corresponding side edge in the width direction of the inner member 10, to the corresponding side edge portion in the width direction of the body-facing surface of the inner member 10. The front and back end portions opposed in the longitudinal direction of the body part are fixed to the body-facing surface of the inner member 10, while the middle area in the longitudinal direction of the body part is not fixed to the body-facing surface of the inner member 10 and stands up toward the body side.

Each three-dimensional gather part 16 is formed of a three-dimensional gathered sheet 17 folded along the free edge of the body part, and three-dimensional gathering elastic members 18 each extending in the longitudinal direction and in an elongate form.

The three-dimensional gathered sheet 17 may be formed of synthetic fibers, such as polyolefin-based including polyethylene or polypropylene, polyester-based, or polyamide-based fibers, recycled fibers, such as rayon or cupra, or natural fibers, such as cotton, and may be nonwoven fabric which has been produced through suitable processing, such as spunbonding, thermal bonding, melt-blowing, or needle punching. In particular, for preventing dampness, nonwoven fabric with a reduced basis weight for improved air-permeability may preferably be used. Further, the three-dimensional gathered sheet 17 may preferably be a water-repelling nonwoven fabric with a coating of a silicone-, paraffin-metal-, or alkyl chromic chloride-based water repelling agent for keeping urine or the like from permeation as well as for preventing rash and improving a touch to the skin (dryness).

The three-dimensional gathering elastic members 18 may be made of a material that is usually used, for example, polystyrene rubber, polyolefin rubber, polyurethane rubber, polyester rubber, polyurethane, polyethylene, polystyrene, styrene-butadiene copolymers, silicone, or polyester. The three-dimensional gathering elastic members, for making them hardly observable from outside, may preferably have a fineness of 925 dtex or less and are arranged at a tension of 150 to 350% and at intervals of 10.0 mm or less. In addition, as shown in dotted lines in FIG. 3, the three-dimensional gathering elastic members 18, under the stretching/contracting force thereof, cause the three-dimensional gather part 16 to stand up inwards, and may be in the form of strings or tapes having a certain width.

First Embodiment

FIG. 6 shows an absorbent body 14 according to the first embodiment. As shown in the figure, the absorbent body 14 has a rectangular ventral section 14A, a rectangular dorsal section 14C, and a crotch section 14B located between the ventral section 14A and the dorsal section 14C.

The crotch section 14B has an inverted-trapezoidal front area 30, a rectangular middle area 31, and a trapezoidal back area 32.

The left side edge of the front area 30 curves backward right from the back end of the left side edge of the ventral section 14A, bulging to the left, extends backward right in a straight line at a specific intersecting angle θ with a longitudinal virtual line L, and then curves backward, bulging to the right, up to the front end of the left side edge of the middle area 31. The straight-line part of the left side edge of the front area 30 is referred to as a left oblique part (a first oblique part in the claims 30A.

The right side edge of the front area 30 curves backward left from the back end of the right side edge of the ventral section 14A, bulging to the right, extends backward left in a straight line at a specific intersecting angle θ with a longitudinal virtual line L, and then curves backward, bulging to the left, up to the front end of the right side edge of the middle area 31. The straight-line part of the right side edge of the front area 30 is referred to as a right oblique part (a first oblique part in the claims 30B.

The left side edge of the middle area 31 extends from the front end to the back end of the left side edge of the middle area 31 in a straight line parallel to the longitudinal virtual line L, whereas the right side edge of the middle area 31 extends from the front end to the back end of the right side edge of the middle area 31 in a straight line parallel to the longitudinal virtual line L. The straight-line part of the left side edge of the middle area 31 is referred to as a left straight part (a straight part in the claims 31A, whereas the straight-line part of the right side edge of the middle area 31 is referred to as a right straight part (a straight part in the claims 31B.

The left side edge of the back area 32 curves backward left from the back end of the left side edge of the middle area 31, bulging to the right, extends backward left in a straight line at a specific intersecting angle β with the longitudinal virtual line L, and then curves backward, bulging to the left, up to the front end of the left side edge of the dorsal section 14C. The straight-line part of the left side edge of the back area 32 is referred to as a left oblique part (a second oblique part in the claims 32A.

The right side edge of the back area 32 curves backward right from the back end of the right side edge of the middle area 31, bulging to the left, extends backward right in a straight line at a specific intersecting angle β with the longitudinal virtual line L, and then curves backward, bulging to the right, up to the front end of the right side edge of the dorsal section 14C. The straight-line part of the right side edge of the back area 32 is referred to as a right oblique part (a second oblique part in the claims 32B.

From the ventral section 14A to the front area 30 of the crotch section 14B, a left slit 40A is provided, extending at a certain longitudinal distance forward from and in parallel to the left oblique part 30A of the front area 30, and a right slit 40B is provided, extending at a certain longitudinal distance forward from and in parallel to the right oblique part 30B of the front area 30.

The front end of the left slit 40A is located in the vicinity of the left side edge of the ventral section 14A, whereas the back end of the left slit 40A is located in the front area 30 of the crotch section 14B and to the right of a virtual line LA extending along the left side edge of the middle area 31 of the crotch section 14B. The front end of the right slit 40B is located in the vicinity of the right side edge of the ventral section 14A, whereas the back end of the right slit 40B is located in the front area 30 of the crotch section 14B and to the left of a virtual line LB extending along the right side edge of the middle area 31 of the crotch section 14B. With this structure, when the wearer moves his left or right leg forward in walking or the like, a great force in the direction orthogonal to the left oblique part 30A or the right oblique part 30B may cause a large deformation in the ventral section 14A and the front area 30 of the crotch section 14B in the direction orthogonal to the left oblique part 30A or the right oblique part 30B, which, however, can be suppressed by the gap in the minor axis direction of the left slit 40A or the right slit 40B being narrowed. Note that the front end of the left slit 40A may be located on the left side edge of the ventral section 14A, and the front end of the right slit 40B may be located on the right side edge of the ventral section 14A. The left slit 40A and the right slit 40B may sometimes be referred to collectively as a pair of slits (a pair of first slits in the claims 40. Further, the pair of slits 40 may be replaced with a pair of low-basis-weight areas where the basis weight of the absorbent material of the absorbent body 14 is lower than the surroundings, or with a pair of compressed areas where the absorbent body 14 is compressed in the thickness direction.

In the middle area 31 of the crotch section 14B, a slit (a second slit in the claims) 41 is provided, extending longitudinally in the central part in the width direction of the middle area 31. The front end of the slit 41 is located in the front of the middle area 31, whereas the back end of the slit 41 is located in the back of the middle area 31. With this structure, when the wearer crosses his legs at a break or the like, a great force in the direction orthogonal to the left straight part 31A and the right straight part 31B may cause a large deformation in the middle area 31 of the crotch section 14B in the direction orthogonal to the left straight part 31A and the right straight part 31B, which, however, can be suppressed by the gap in the minor axis direction of the slit 41 being narrowed. Note that the slit 41 may be replaced with a low-basis-weight area where the basis weight of the absorbent material of the absorbent body 14 is lower than the surroundings, or with a compressed area where the absorbent body 14 is compressed in the thickness direction. Further, the front end of the slit 41 may be extended forward of the middle area 31 up to the front area 30, whereas the back end of the slit 41 may be extended backward of the middle area 31 down to the back area 32. As used herein, the central part in the width direction of the middle area 31 means, when each of the side edges opposed in the width direction of the middle area 31 is formed arcuately, the middle of the narrowest part in the width direction of the middle area 31.

From the middle area 31 to the back area 32 of the crotch section 14B, a left slit 42A is provided, extending at a certain longitudinal distance backward from and in parallel to the left oblique part 32A of the back area 32, and a right slit 42B is provided, extending at a certain longitudinal distance backward from and in parallel to the right oblique part 32B of the back area 32.

The front end of the left slit 42A is connected to the back end of the slit 41, whereas the back end of the left slit 42A is located in the back area 32 of the crotch section 14B and to the right of the virtual line LA extending along the left side edge of the middle area 31 of the crotch section 14B. The front end of the right slit 42B is connected to the back end of the slit 41, whereas the back end of the right slit 42B is located in the back area 32 of the crotch section 14B and to the left of the virtual line LB extending along the right side edge of the middle area 31 of the crotch section 14B. With this structure, when the wearer moves his left or right leg backward in walking or the like, a great force in the direction orthogonal to the left oblique part 32A or the right oblique part 32B cause a large deformation in the back area 32 of the crotch section 14B in the direction orthogonal to the left oblique part 32A or the right oblique part 32B, which, however, may be suppressed by the gap in the minor axis direction of the left slit 42A or the right slit 42B being narrowed. Further, the bodily waste absorbed in the absorbent body 14 may be kept from leaking out through the back ends of the left slit 42A or the right slit 42B. In addition, the dorsal section 14C of the absorbent body 14 may effectively be caused to fit on the dorsal portion of the wearer.

The left slit 42A may be more gradual than the left oblique part 32A, i.e., the intersecting angle between the left slit 42A and the virtual line L may be made smaller than the intersecting angle between the left oblique part 32A and the virtual line L, whereas the right slit 42B may be more gradual than the right oblique part 32B, i.e., the intersecting angle between the right slit 42B and the virtual line L may be made smaller than the intersecting angle between the right oblique part 32B and the virtual line L. The left slit 42A and the right slit 42B may sometimes be referred to collectively as a pair of slits (a pair of third slits in the claims 42. Further, the pair of slits 42 may be replaced with a pair of low-basis-weight areas where the basis weight of the absorbent material of the absorbent body 14 is lower than the surroundings, or with a pair of compressed area where the absorbent body 14 is compressed in the thickness direction.

In the dorsal section 14C, a left slit 43A is provided, extending in parallel to the right oblique part 32B at a certain longitudinal distance backward from the left oblique part 32A of the back area 32 of the crotch section 14B, and a right slit 43B is provided, extending in parallel to the left oblique part 32A at a certain longitudinal distance backward from the right oblique part 32B of the back area 32 of the crotch section 14B.

The front end of the left slit 43A is located in the front of the dorsal section 14C and backward of the left slit 42A, whereas the back end of the left slit 43A is located in the back of the dorsal section 14C and to the right of the virtual line LB extending along the right side edge of the middle area 31 of the crotch section 14B. The front end of the right slit 43B is located in the front of the dorsal section 14C and backward of the right slit 42B, whereas the back end of the right slit 43B is located in the back of the dorsal section 14C and to the left of the virtual line LA extending along the left side edge of the middle area 31 of the crotch section 14B.

A virtual line extending along the longitudinal axis of the left slit 43A crosses a virtual line extending along the longitudinal axis of the right slit 43B at the center the width direction of the dorsal section 14C. Each of the left slit 43A and the right slit 43B has discontinuous in the middle part of the longitudinal axis. With this structure, when the wearer moves his left or right leg back and forth in walking or the like, a great force in the direction orthogonal to the left oblique part 32A or the right oblique part 32B causes a large deformation in the dorsal section 14C in the direction orthogonal to the left oblique part 32A or the right oblique part 32B, which, however, may be suppressed by the gap in the minor axis direction of the left slit 43A or the right slit 43B being narrowed. In addition, the dorsal section 14C of the absorbent body 14 may be effectively caused to fit on the dorsal portion of the wearer.

Slits may be formed in the middle parts of the longitudinal axes of the left slit 43A and the right slit 43B. The left slit 43A and the right slit 43B may sometimes be referred to collectively as a pair of slits (a pair of fourth slits in the claims 43. Further, the pair of slits 43 may be replaced with a pair of low-basis-weight area where the basis weight of the absorbent material of the absorbent body 14 is lower than the surroundings, or with a pair of compressed area where the absorbent body 14 is compressed in the thickness direction.

The width of the slits is the largest in the slit 41, the width of the slits 42 is half the width of the slit 41, and the width of the slits 40 and the width of the slits 43 are equal and smaller than the width of the slit 41 and larger than the width of the slits 42. For example, the width of the slit 41 may be 14 mm, the width of the slits 42 may be 7 mm, and the width of the slits 40 and the width of the slits 43 are both 10 mm. In this way, the deformation of the crotch section 14B of the absorbent body 14, which deforms the most when the wearer walks or the like, may be suppressed.

Second Embodiment

FIG. 7 shows an absorbent body 14 according to the second embodiment. Note that the same parts and areas are referred to by the same reference numerals as in the first embodiment, and explanations thereof are omitted.

As shown in FIG. 7, a rectangular elastic member 50 stretchable in its width direction is provided on the surface of the absorbent body 14 opposite from its body-facing surface at a position facing to the slits 40, a rectangular elastic member 51 stretchable in its width direction is provided on the surface of the absorbent body 14 opposite from its body-facing surface at a position facing to the slit 41 and the slits 42, a rectangular elastic member 52 stretchable in its width direction is provided on the surface of the absorbent body 14 opposite from its body-facing surface at a position facing to the slits 42, and a rectangular elastic member 53 stretchable in its width direction is provided on the surface of the absorbent body 14 opposite from its body-facing surface at a position facing to the slits 43. In this way, the width of the slit 41 or the like may be narrowed easily to promptly suppress the deformation of the absorbent body 14 while the wearer is walking or the like. Note that the elastic members 50 and 53 may be substituted with elastic sheets 24 of the outer member 20 to be discussed later.

Third Embodiment

FIG. 8 shows an absorbent body 14 according to the third embodiment. The same parts and areas are referred to by the same reference numerals as in the first embodiment, and explanations thereof are omitted.

As shown in FIG. 8, the front end of the slit 41 is located in the front of the middle area 31 of the crotch section 14B, whereas the back end of the slit 41 is located in the back of the back area 32 of the crotch section 14B. With this structure, when the wearer crosses his legs at a break or the like, the width in the minor axis direction of the slit 41 is narrowed to suppress the deformation of the middle area 31 and the back area 32 of the crotch section 14B.

The front end of the left slit 42A is located in the front of the back area 32 of the crotch section 14B and to the left of the slit 41, whereas the back end of the left slit 42A is located in the back area 32 of the crotch section 14B and to the right of the virtual line LA extending along the left side edge of the middle area 31 of the crotch section 14B. The front end of the right slit 42B is located in the front of the back area 32 of the crotch section 14B and to the right of the slit 41, whereas the back end of the right slit 42B is located in the back area 32 of the crotch section 14B and to the left of the virtual line LB extending along the right side edge of the middle area 31 of the crotch section 14B. With this structure, when the wearer moves his left or right leg backward in walking or the like, the width in the minor axis direction of the left slit 42A or the right slit 42B is narrowed to suppress the deformation of the back area 32 of the crotch section 14B.

Fourth Embodiment

FIG. 9 shows an absorbent body 14 according to the fourth embodiment. Note that the same parts and areas are referred to by the same reference numerals as in the first embodiment, and explanations thereof are omitted.

As shown in FIG. 9, the front end of the left slit 40A is located in the vicinity of the left side edge of the ventral section 14A, whereas the back end of the left slit 40A is located in the middle area 31 of the crotch section 14B and connected to the front end of the slit 41. The front end of the right slit 40B is located in the vicinity of the right side edge of the ventral section 14A, whereas the back end of the right slit 40B is located in the middle area 31 of the crotch section 14B and connected to the front end of the slit 41. With this structure, when the wearer moves his left or right leg forward in walking or the like, the width in the minor axis direction of the left slit 40A or the right slit 40B is narrowed to suppress the deformation of the ventral section 14A and the front area 30 and the middle area 31 of the crotch section 14B.

The front end of the slit 41 is connected to the back ends of the left slit 40A and the right slit 40B, whereas the back end of the slit 41 is located in the back of the back area 32 of the crotch section 14B. With this structure, when the wearer crosses his legs at a break or the like, the width in the minor axis direction of the slit 41 is narrowed to suppress the deformation of the middle area 31 and the back area 32 of the crotch section 14B.

The front end of the left slit 43A is located in the front of the dorsal section 14C and backward of the left slit 42A, whereas the back end of the left slit 43A is located in the back of the dorsal section 14C and to the right of the virtual line LB extending along the right side edge of the middle area 31 of the crotch section 14B. The front end of the right slit 43B is located in the front of the dorsal section 14C and backward of the right slit 42B, whereas the back end of the right slit 43B is located in the back of the dorsal section 14C and to the left of the virtual line LA extending along the left side edge of the middle area 31 of the crotch section 14B.

A virtual line extending along the longitudinal axis of the left slit 43A crosses a virtual line extending along the longitudinal axis of the right slit 43B at the center in the width direction of the dorsal section 14C. With this structure, when the wearer moves his left or right leg back and forth in walking or the like, the width in the minor axis direction of the left slit 43A or the right slit 43B is narrowed to suppress the deformation of the dorsal section 14C in the direction orthogonal to the left slit 43A or the right slit 43B.

<Outer Member>

As shown in FIGS. 1 and 2, the outer member 20 has a front body section F facing the ventral portion of the wearer, and a back body section B facing the dorsal portion of the wearer. The front body section F and the back body section B are formed separately. Note that the front body section F and the back body section B may be formed integrally.

The front body section F and the back body section B are joined together along their side portions opposed in the width direction by thermal melt-bonding or the like to form opposed side seals 21. In this way, a waist opening for receiving the waist of the wear therein and a pair of right and left leg openings for receiving the legs of the wearer therein are formed.

The outer member 20 has waist zones N which are front and back zones in the longitudinal direction having side seals 21, and a leg opening zone M connecting the front and back waist zones N. Further, each waist zone N conceptually has a waist area W located at the waist opening, and an under-waist area U located closer to the leg opening zone M than the waist area W.

The outer member 20 is composed of an inner sheet 22 arranged on the body-facing side, an outer sheet 23 arranged on the side opposite from the body-facing side, and elastic sheets 24 stretchable in the width direction and held between the inner sheet 22 and the outer sheet 23. Each of the end portions opposed in the longitudinal direction of the outer sheet 23 is folded onto the body-facing side of the inner sheet 22.

As shown in FIG. 10, each elastic sheet 24 has apertures 25 formed at predetermined intervals in the longitudinal and width directions. The inner sheet 22 and the outer sheet 23 are joined via bonded areas 26 each formed by ultrasonic melt-bonding on the inner periphery of each aperture 25. In this way, irregularities are formed on the body-facing surface and the surface opposite therefrom of the outer member 20, when the diaper is worn, so that the outer member 20 may be caused to fit the wearer.

The inner sheet 22 and the outer sheet 23 are preferably nonwoven fabric excellent in air-permeability and flexibility, like the top sheet 11.

The elastic sheet 24 may be an elastic film or stretchable nonwoven fabric, as long as it is a thermoplastic resin sheet having elasticity. In particular, the elastic sheet 24 preferably has a tensile strength in the width direction of 8 to 25 N/35 mm, a tensile strength in the longitudinal direction of 5 to 20 N/35 mm, a tensile elongation in the width direction of 450 to 1050%, and a tensile elongation in the longitudinal direction of 450 to 1400%. The thickness of the elastic sheet is not particularly limited, and may preferably be about 20 to 40 μm.

<Explanation of Terms in the Specification>

The following terms appearing in the present specification shall have the following meanings unless otherwise specified herein.

The "front body section" and the "back body section" refer to the front side section and the back side section, respectively, of the widthwise centerline passing the middle of the front-back direction of an underpants-type disposable diaper. The "crotch section" refers to a front-back directional range containing the center of the front-back direction of an underpants-type disposable diaper and, when the absorbent body has the narrowed portion, refers to a front-back directional range containing the narrowed portion.

The "stretch rate" refers to a value with respect to the natural length being 100%. For example, a 200% stretch rate is synonymous with stretch in two folds.

The "thickness" is automatically measured using an automatic thickness meter (KES-G5 handy compression tester program) under a load of 0.098 $N/cm^2$ with the compression area of 2 $cm^2$.

The "tensile strength" and the "tensile elongation (breaking elongation)" refers to a value determined in accordance with JIS K7127: 1999 "Plastics—Determination of tensile properties", with the initial chuck distance (distance between the marked lines) of 50 mm at a tension rate of 300 mm/min, except that the test specimen is in the form of a rectangle of 35 mm wide and 80 mm long. The tensile tester may be, for example, AUTOGRAPH AGS-G100N manufactured by SHIMADZU CORPORATION.

The "spread state" refers to the state in which an article is spread flatly without contraction or slack.

The size of each part refers to the size not in the natural length state, but in the spread state, unless otherwise specified.

A test or measurement shall be, in the absence of description about environmental conditions, performed in a laboratory or in apparatus under the standard conditions (at a temperature of 23.1° C. and a relative humidity of 50.2% in the testing location).

INDUSTRIAL APPLICABILITY

The present invention is applicable to disposable diapers.

DESCRIPTION OF REFERENCE NUMERALS

10: inner member
11: top sheet
12: under sheet
14: absorbent body
14A: ventral section
14B: crotch section
14C: dorsal section
20: outer member
30: front area
30A: left oblique part (first oblique part)
30B: right oblique part (first oblique part)
31: middle area
31A: left straight part
31B: right straight part

32: back area
32A: left oblique part
32B: right oblique part
40: slit (first slit)
41: slit (second slit)
42: slit (third slit)
43: slit (fourth slit)
50: elastic member
51: elastic member
52: elastic member
53: elastic member

The invention claimed is:

1. A disposable diaper comprising:

an inner member having a liquid-permeable top sheet, a liquid-impermeable under sheet, and an absorbent body interposed between the top sheet and the under sheet, and an outer member stretchable in its width direction and fixed on a surface of the inner member opposite to another surface thereof facing a body of a wearer, wherein the absorbent body, as seen in plan view, has a rectangular ventral section facing a ventral portion of the wearer, a rectangular dorsal section facing a dorsal portion of the wearer, and a crotch section connecting the ventral section and the dorsal section, wherein each of side edges opposed in a width direction of a front area of the crotch section has a first oblique part extending from front backward and inward in the width direction, wherein each of side edges opposed in a width direction of a back area of the crotch section has a second oblique part extending from back forward and inward in the width direction, wherein each of side edges opposed in a width direction of a middle area of the crotch section has a straight part extending from a back end of the first oblique part to a front end of the second oblique part, wherein a pair of first slits is provided from the ventral section to the front area of the crotch section in their side portions opposed in their width direction, at a distance from and in parallel to the first oblique parts, wherein a second slit is provided in parallel to the straight parts, in a central part in the width direction of the middle area of the crotch section, wherein a pair of third slits is provided at a distance from the second oblique parts, in the back part of the crotch section in its side portions opposed in the width direction, with a back end of each third slit located laterally outwards of its front end in the width direction, wherein a pair of fourth slits is provided crossing each other and in parallel to the second oblique parts, in a middle area in a width direction of the dorsal section, wherein back ends of the first slits are located inwards of the straight parts in a width direction of the absorbent body, and wherein front ends of the fourth slits are located at a longitudinal distance from the back ends of the third slits.

2. The disposable diaper according to claim 1, wherein a point of crossing of the fourth slits is located at a center of the width direction of the dorsal section, and wherein a length of each fourth slit backward of the point of crossing is longer than a length of the fourth slit forward of the point of crossing.

3. The disposable diaper according to claim 2, wherein a width in a minor axis direction of the second slit is larger than that of the first slits, that of the third slits, and that of the fourth slits.

4. The disposable diaper according to claim 2, wherein the front ends of the third slits are connected to a back end of the second slit.

5. The disposable diaper according to claim 2, wherein an elastic member stretchable in its width direction is provided on a surface of the absorbent body opposite to another surface facing the body of the wearer, in at least one of positions facing to the first slits, the second slit, the third slits, and the fourth slits.

6. The disposable diaper according to claim 1, wherein a width in a minor axis direction of the second slit is larger than that of the first slits, that of the third slits, and that of the fourth slits.

7. The disposable diaper according to claim 6, wherein the front ends of the third slits are connected to a back end of the second slit.

8. The disposable diaper according to claim 6, wherein an elastic member stretchable in its width direction is provided on a surface of the absorbent body opposite to another surface facing the body of the wearer, in at least one of positions facing to the first slits, the second slit, the third slits, and the fourth slits.

9. The disposable diaper according to claim 1, wherein the front ends of the third slits are connected to a back end of the second slit.

10. The disposable diaper according to claim 1, wherein an elastic member stretchable in its width direction is provided on a surface of the absorbent body opposite to another surface facing the body of the wearer, in at least one of positions facing to the first slits, the second slit, the third slits, and the fourth slits.

* * * * *